(12) United States Patent
Janakiraman

(10) Patent No.: US 6,906,090 B1
(45) Date of Patent: Jun. 14, 2005

(54) COMPOSITIONS AND METHODS FOR TREATING MYCOBACTERIAL DISEASES

(75) Inventor: Ramachandran Janakiraman, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/284,516

(22) PCT Filed: Mar. 4, 1999

(86) PCT No.: PCT/SE99/00319

§ 371 (c)(1),
(2), (4) Date: Apr. 14, 1999

(87) PCT Pub. No.: WO99/44608

PCT Pub. Date: Sep. 10, 1999

(30) Foreign Application Priority Data

Mar. 6, 1998 (IN) .......................................... 464/MAS/98
Apr. 20, 1998 (SE) ............................................... 9801370

(51) Int. Cl.⁷ ...................... A61K 31/415; A61K 31/40; A61K 31/445; A61K 31/55
(52) U.S. Cl. .................... 514/387; 514/418; 514/217.8; 514/217.9; 514/321; 514/322; 514/323; 540/575; 540/602; 540/603; 544/370; 544/373; 546/199; 546/201; 548/306.4; 548/486; 548/485

(58) Field of Search ................................. 514/387, 418, 514/217.8, 217.9, 321, 322, 323; 540/575, 602, 603; 544/370, 373; 546/199, 201; 548/306.4, 486, 485

(56) References Cited

U.S. PATENT DOCUMENTS 4,382,934 A * 5/1983 Teraji et al. ............ 514/254.09
5,585,378 A * 12/1996 Boar et al. ............. 514/254.09

FOREIGN PATENT DOCUMENTS

| EP | 0432648 | | 6/1991 |
| EP | 0503349 | | 9/1992 |
| WO | 9312085 | | 6/1993 |
| WO | WO 93/12085 | * | 6/1993 |
| WO | 9429272 | | 12/1994 |
| WO | WO 94/29272 | * | 12/1994 |

OTHER PUBLICATIONS

Piscopo et al., Boll. Soc. It. Biol. Sper. 52:1449–1455 (1986).
Verma et al., Indian J. Chem. 21B: 775–777 (1982).
Movrin et al., Pharmazie 34: 231–232 (1979).

* cited by examiner

Primary Examiner—D. Margaret Seaman
(74) Attorney, Agent, or Firm—White & Case LLP

(57) ABSTRACT

The invention provides the use of certain isatin and oxindole derivatives in the preparation of a medicament for use in the treatment of mycobacterial disease.

7 Claims, No Drawings

COMPOSITIONS AND METHODS FOR TREATING MYCOBACTERIAL DISEASES

The present invention relates to the use of certain isatin and oxindole derivatives in the treatment of mycobacterial diseases, particularly those diseases caused by pathogenic mycobacteria such as *Mycobacterium tuberculosis, M. bovis, M. avium* and *M. marinum*.

Tuberculosis is still a major public health problem affecting nearly all parts of the world. Based on skin test reactivity it has been estimated that about one-third of the world's population, i.e., 1.7 billion people, are infected with *Mycobacterium tuberculosis*. Despite the availability of effective chemotherapies, it is responsible for three million deaths and from eight to ten million new cases annually and thus remains the leading cause of death world-wide due to a single infectious agent: 26% of all preventable deaths, 7% of all deaths. According to the World Health Organisation, 450,000 deaths per year due to tuberculosis in developing countries occur in children under fifteen years of age, and the disease mostly affects the younger, more productive adults.

There are five front-line drugs known to be highly effective against *M. tuberculosis* and five second-line drugs that can be used when resistance to one or more of the front-line drugs is detected. The preferred mode of treatment for tuberculosis is the short course chemotherapy in which there are two phases. The first phase consists of a daily regimen for two months with isoniazid (300 mg), rifampicin (600 mg), pyrazinamide (3 g) and ethambutol (1.5 g). The second phase or the continuation phase consists of a daily regimen for the next four months with isoniazid and rifampicin. Although infection with drug-sensitive strains of *M. tuberculosis* can be effectively cured with the short course chemotherapy, the cure rate is very poor in most countries due to poor compliance which is reflective of the long duration of therapy.

The situation is further complicated by the rapid emergence of multi-drug resistant tuberculosis (MDR-TB) strains. For example, in certain populations, the incidence of resistance to isoniazid is as high as 26% and the resistance to rifampicin is about 15%. Prior to 1984, about 10% of tubercle bacilli isolated from patients in the United States were resistant to at least one single mycobacterial drug. By 1984, this figure had risen to 52%, of which over half (32%) were resistant to more than one drug (MDR-TB). Ten percent of the recorded MDR-TB cases have occurred in previously healthy people whose mortality rate –70 to 90%–has been nearly the same as that of immunosuppressed individuals with MDR-TB. The number of cases of MDR-TB has doubled since 1984 and in many of them the tubercle bacilli are resistant to both isoniazid and rifampicin. The median interval between diagnosis of MDR-TB and death is only four weeks and therefore MDR-TB demands a shorter response time between diagnosis and appropriate commencement of treatment. However, MDR-TB is difficult to treat as such since most patients do not respond very well to the second-line drugs and the cost of alternate treatment procedures, including hospitalisation and possibly surgery, increases the cost to as much as ten times the cost of traditional treatment.

Thus, there is an urgent medical need to identify new drugs with significant therapeutic activity against single- or multiple-drug resistant strains of *M. tuberculosis* and with pharmacokinetic properties that permit reduced dosing which will in turn encourage better compliance.

WO 93/12085 and WO 94/29272 describe two classes of isatin and oxindole derivatives which function as acetylcholinesterase inhibitors and which have application as pharmaceuticals in the treatment of cognitive dysfunctions such as Alzheimer's disease, senile dementia, Parkinson's disease, Down's syndrome and Huntington's chorea.

In accordance with the present invention, there is provided the use of a compound of general formula

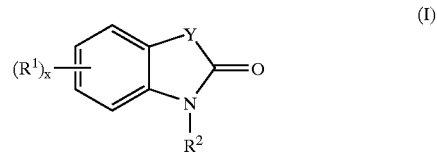

(I)

wherein x represents 0 or 1, $R^1$ represents a 3- to 7-membered (hetero)cycloalkyl group or alkyl group optionally substituted by one or more halogen atoms, a group

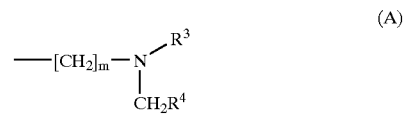

(A)

wherein m represents an integer from 3 to 7, $R^3$ represents a $C_1$–$C_6$ alkyl group and $R^4$ represents a cyclohexyl or phenyl group optionally substituted by one or more substituents selected from the group consisting of a halogen atom, $C_1$–$C_6$ alkyl and $C_1$–$C_6$ alkoxy group, or a group

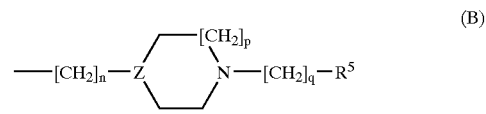

(B)

wherein n represents an integer from 2 to 4, p and q independently represent an integer from 1 to 2, Z represents N or CH and $R^5$ represents a cyclohexyl or phenyl group optionally substituted by one or more substituents selected from the group consisting of a halogen atom, $C_1$–$C_6$ alkyl and $C_1$–$C_6$ alkoxy group,.

or a pharmaceutically-acceptable salt or solvate thereof in the manufacture of a medicament for use in the treatment of a mycobacterial disease, in particular tuberculosis.

Preferably Y in formula (I) represents a group >C=O.

Preferably $R^1$ represent a 5- to 7-membered (hetero) cycloalkyl group (e.g. a cyclopentyl, cyclohexyl, cycloheptyl, pyrrolidinyl, imidazolinyl, pyrazolidinyl, piperidinyl, piperazinyl or morpholinyl group) or a phenyl group. Most preferably $R^1$ represents a cyclopentyl, cyclohexyl, cycloheptyl or 1-piperidinyl group. Particularly advantageous compounds of formula (I) to use are those in which the group $R^1$ is located in the 5- or 7-position of the bicyclic ring system.

$R^2$ represents either a $C_1$–$C_{12}$, preferably $C_4$–$C_{12}$, alkyl group (e.g. a methyl, ethyl, propyl, butyl, 2-methylpropyl, pentyl, hexyl, heptyl, octyl, nonyl, decyl, undecyl or dodecyl group); a group (A) as defined above in which m represents an integer from 3 to 7, preferably 4 or 5, $R^3$ represents a $C_1$–$C_6$ alkyl group (e.g. a methyl, propyl, butyl, pentyl, hexyl or especially ethyl group) and $R^4$ represents a cyclohexyl or, preferably, phenyl group optionally substituted by one or more, e.g. one, two, three or four, substituents selected from the group consisting of a halogen atom (e.g. fluorine, chlorine or bromine), $C_1$–$C_6$ alkyl (e.g. methyl, ethyl or propyl) and $C_1$–$C_6$ alkoxy (e.g. methoxy, ethoxy or propoxy) group; or a group (B) as defined above in which n represents an integer from 2 to 4, preferably 2, p and q independently represent an integer of 2 or preferably 1, Z represents N or CH and $R^5$ represents a cyclohexyl or, preferably, phenyl group optionally substituted by one or more, e.g. one, two, three or four, substituents selected from the group consisting of a halogen atom (e.g. fluorine, chlorine or bromine), $C_1$–$C_6$ alkyl (e.g. methyl, ethyl or propyl) and $C_1$–$C_6$ alkoxy (e.g. methoxy, ethoxy or propoxy) group.

In the present invention, it is preferred to use a compound being:

5-Cyclohexyl-1-[2-[1-(phenylmethyl)-4-piperidinyl]ethyl]-1H-indole-2,3-dione;
7-Cycloheptyl-1-[2-[4-(phenylmethyl)-1-piperazinyl]ethyl]-1H-indole-2,3-dione;
5-Cyclohexyl-1-(5-(N-ethyl-N-phenylethylamino)pentyl)-1H-indole-2,3-dione;
5-Cyclohexyl-1,3-dihydro-1-[2-[1-(phenylmethyl)-4-piperidinyl]ethyl]-2H-indol-2-one;
1-(4-(N-Ethyl-N-phenylmethylamino)butyl)-1H-indole-2,3-dione;
5-Phenyl-1-[2-[4-(phenylmethyl)-1-piperazinyl]ethyl]-1H-indole-2,3-dione;
7-Cyclopentyl-1-[2-[4-phenylmethyl)-1-piperazinyl]ethyl]-1H-indole-2,3-dione;
5-(1-Piperidinyl)-1-[2-[4-(phenylmethyl)-1-piperazinyl]ethyl]-1H-indole-2,3-dione;
1-(4-Bromobutyl)-5-cyclohexyl-1H-indole-2,3-dione;
1-Nonyl-7-phenyl-1H-indole-2,3-dione;
1-Heptyl-7-phenyl-1H-indole-2,3-dione;
1-Octyl-7-phenyl-1H-indole-2,3-dione;
1-Decyl-7-phenyl-1H-indole-2,3-dione;
1-Undecyl-7-phenyl-1H-indole-2,3-dione;
1-Pentyl-7-phenyl-1H-indole-2,3-dione;
1-Butyl-7-phenyl-1H-indole-2,3-dione;
1-(2-Methylpropyl)-7-phenyl-1H-indole-2,3-dione;
1-Hexyl-7-phenyl-1H-indole-2,3-dione;
1-Dodecyl-7-phenyl-1H-indole-2,3-dione; or
1-(4-Bromobutyl)-7-phenyl-1H-indole-2,3-dione;

or a pharmaceutically-acceptable salt or solvate thereof.

The compounds of formula I may be prepared by processes known in the art or by processes analogous to those known in the art, for example, as described in WO 93/12085 and WO 94/29272.

Some of the compounds of formula (I) above are novel. Therefore, the present invention further provides a compound of the general formula

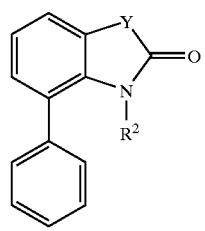

(I')

wherein Y and $R^2$ are as hereinbefore defined, or a pharmaceutically-acceptable salt or solvate thereof.

The present invention still further provides a process for preparing a compound of formula (I') which comprises reacting a compound of formula

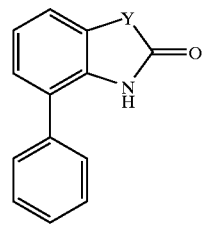

(II)

in which Y is as hereinbefore defined, with a compound of general formula (III), $R^2$-L, where L represents a leaving group such as a halogen atom and $R^2$ is as hereinbefore defined, and optionally thereafter forming a pharmaceutically-acceptable salt or solvate thereof.

The process may conveniently be carried out in a solvent such as dimethylformamide or tetrahydrofuran and in the presence of a base such as triethylamine, anhydrous potassium carbonate or sodium hydride. The process will suitably be carried out at a temperature in the range from 0 to 100° C.

It will be appreciated by those skilled in the art that in the process of the present invention certain functional groups in the intermediate compounds may need to be protected by protecting groups. Thus, the final stage in the preparation of the compounds of formula (I') may involve the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991). Interscience (1191).

The compounds of formula (I) or (I') may be converted to a pharmaceutically-acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) or (I') are capable of existing in stereoisomeric forms. It will be understood that the invention encompasses all geometric and optical isomers of the compounds of formula (I) or (I') and mixtures thereof including racemates. Tautomers and mixtures thereof also form an aspect of the present invention.

The compounds according to the present invention are advantageous in that they possess bactericidal activity against mycobacteria, particularly pathogenic mycobacteria such as *Mycobacterium tuberculosis, M. bovis, M. avium* and *M. marinum*. Accordingly, in another aspect, the invention provides a method of treating a patient suffering from, or at risk of, a mycobacterial disease, which comprises administering to the patient a therapeutically effective amount of a compound of formula (I) or (I'), or a pharmaceutically-acceptable salt or solvate thereof, as defined above.

The compounds of formula (I) or (I') and pharmaceutically-acceptable salts and solvates thereof may be used on their own but will generally be administered in the form of a pharmaceutical composition in which the formula (I) or (I') compound/salt/solvate (active ingredient) is in association with a pharmaceutically-acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically-acceptable adjuvant, diluent or carrier, all percentages by weight being based on total composition. The pharmaceutical composition may additionally contain another anti-tubercular agent and/or various other ingredients known in the art, for example, a lubricant, stabilising agent, buffering agent, emulsifying agent, viscosity-regulating agent, surfactant, preservative, flavouring or colorant.

Thus, the present invention also provides a pharmaceutical composition comprising a compound of formula (I'), or a pharmaceutically-acceptable salt or solvate thereof, as hereinbefore defined in association with a pharmaceutically-acceptable adjuvant, diluent or carrier.

The invention further provides a process for the preparation of a pharmaceutical composition of the invention which comprises mixing a compound of formula (I'), or a pharmaceutically-acceptable salt or solvate thereof, as hereinbefore defined with a pharmaceutically-acceptable adjuvant, diluent or carrier.

The daily dosage of formula (I) or (I') compound administered will, of course, vary with the compound employed, the mode of administration, the treatment desired and the mycobacterial disease indicated. However, in general, satisfactory results will be obtained when the compound of formula (I) or (I') is administered at a daily dosage not exceeding 1 g, e.g. in the range from 10 to 50 mg/kg body weight.

The compounds according to the invention may be administered systemically, e.g. by oral administration in the form of tablets, capsules, syrups, powders or granules, or by parenteral administration in the form of solutions or suspensions.

The present invention will be further illustrated with reference to the following examples.

EXAMPLE 1

5-Cyclohexyl-1-[2-[1-(phenylmethyl)-4-piperidinyl] ethyl]-1H-indole-2,3-dione

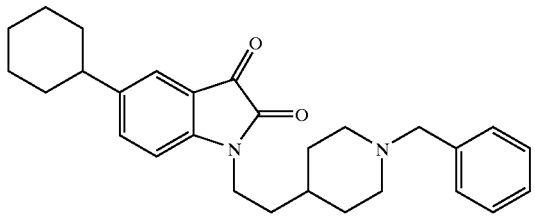

The title compound was prepared as described in Example 104 of WO 93/12085.

EXAMPLE 2

7-Cycloheptyl-1-[2-[4-(phenylmethyl)-1-piperazinyl]ethyl]-1H-indole-2,3-dione

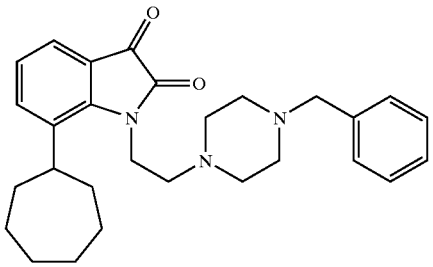

The title compound was prepared as described in Example 63 of WO 93/12085.

EXAMPLE 3

5-Cyclohexyl-1-(5-(N-ethyl-N-phenylmethylamino) pentyl)-1H-indole-2,3-dione

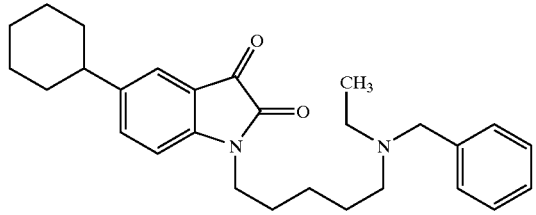

The title compound was prepared as described in Example 22 of WO 94/29272.

EXAMPLE 4

5-Cyclohexyl-1,3-dihydro-1-[2-[1-(phenylmethyl) 4-piperidinyl]ethyl]-2H-2H-indol-2-one

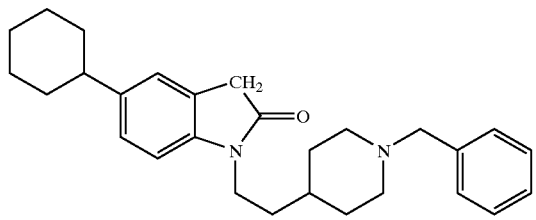

The title compound was prepared as described in Example 107 of WO 931/2085.

EXAMPLE 5

1-(4-(N-Ethyl-N-phenylmethylamino)butyl)-1H-indole-2,3-dione

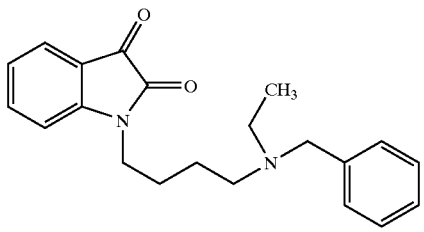

The title compound was prepared as described in Example 19 of WO 94/29272.

EXAMPLE 6

5-Phenyl-1-[2-[4-(phenylmethyl)-1-perazinyl]ethyl]-1H-indole-2,3-dione

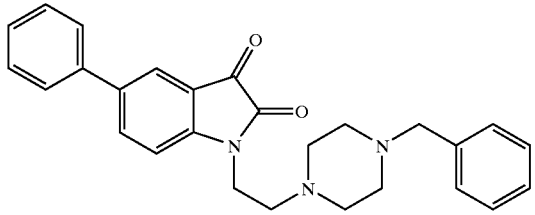

The title compound was prepared as described in Example 97 of WO 93/12085.

EXAMPLE 7

7-Cyclopentyl-1-[2-[4-(phenylmethyl)-1-piperazinyl]ethyl]-1H-indole-2,3-dione

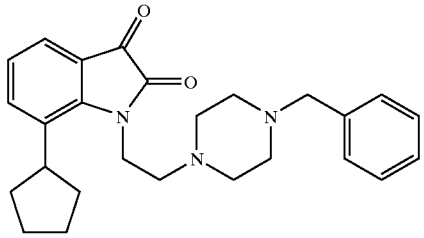

The tide compound was prepared as described in Example 61 of WO 93/12085.

EXAMPLE 8

5-(1-Piperidinyl)-1-[2-[4-(phenylmethyl)-1-piperazinyl]ethyl]-1H-indole-2,3-dione

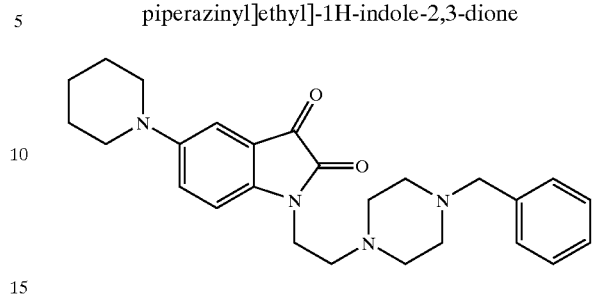

The title compound was prepared in a manner analogous to Example 14 of WO 93/12085 but using 5-(1-piperidinyl)-1H-indole-2,3-dione.

EXAMPLE 9

1-(4-Bromobutyl)-5-cyclohexyl-1H-indole-2,3-dione

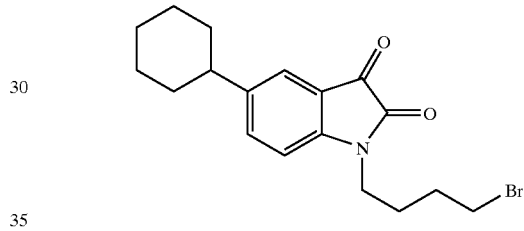

The title compound was prepared as described in Example 29 of WO 94/29272.

EXAMPLE 10

1-Nonyl-7-phenyl-1H-indole-2,3-dione

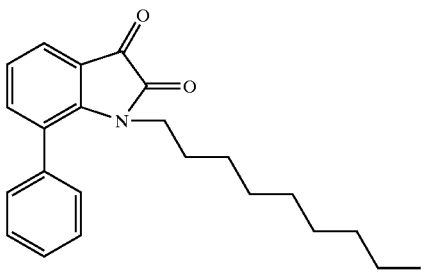

The title compound was prepared in a manner similar to the process step described in the text from Page 7, line 34 to Page 8, line 5 of WO 94/29272 but using a haloalkane such as 1-bromononane together with 7-phenyl-1H-indole-2,3-dione.

$^1$H NMR: δ0.7 (2H, p), 0.9 (3H, t), 0.9–1.3 (12H, m), 3.4 (2H, dd), 7.1 (1H, t), 7.3–7.5 (6H, m), 7.6 (1H, d).

EXAMPLE 11

1-Heptyl-7-phenyl-1H-indole-2,3-dione

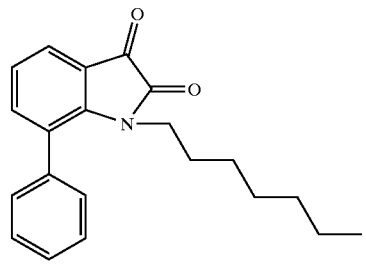

The title compound was prepared as described in Example 10 above except that 1-bromoheptane was used.

$^1$H NMR: δ 0.7 (2H, p), 0.9 (3H, t), 0.9–1.3 (8H, m), 3.4 (2H, dd), 7.1 (1H, t), 7.3–7.5(6H, m), 7.6 (1H, d).

EXAMPLE 12

1-Octyl-7-phenyl-1-H-indole-2,3-dione

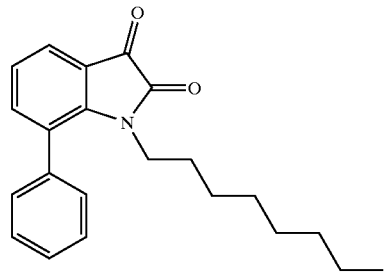

The title compound was prepared as described in Example 10 above except that 1'-bromooctane was used.

$^1$H NMR: δ 0.7 (2H, p), 0.9 (3H, t), 0.9–1.3 (10H, m), 3.4 (2H, dd), 7.1 (1H, t), 7.3–7.5(6H, m), 7.6 (1H, d).

EXAMPLE 13

1-Decyl-7-phenyl-1-H-indole-2,3-dione

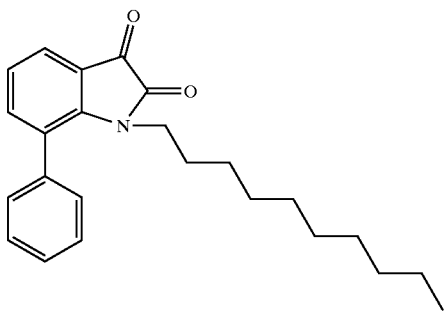

The title compound was prepared as described in Example 10 above except that 1-bromodecane was used.

$^1$H NMR: δ 0.7 (2H, p), 0.9 (3H, t), 0.9–1.3 (14H, m), 3.4 (2H, dd), 7.1 (1H, t), 7.3–7.5 (6H, m), 7.6 (1H, d).

EXAMPLE 14

1-Undececyl-7-phenyl-1-H-indole-2,3-dione

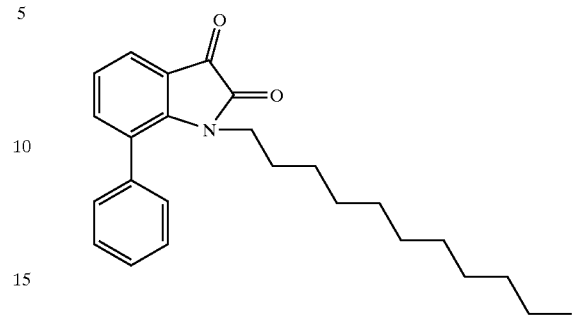

The title compound was prepared as described in Example 10 above except that 1-bromoundecane was used.

$^1$H NMR: δ 0.7 (2H, p), 0.9 (3H, t), 0.8–1.3 (16H, m), 3.3 (2H, dd), 7.1 (1H, t), 7.3–7.5(6H, m), 7.6 (1H, d).

EXAMPLE 15

1-Pentyl-7-phenyl-1H-indole-2,3-dione

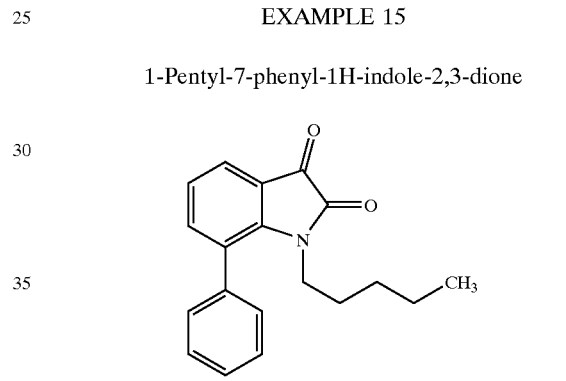

The title compound was prepared as described in Example 10 above except that 1-bromopentane was used.

$^1$H NMR: δ 0.6–0.8 (5H, m), 0.9–1.1 (2H, m), 1.1–1.3 (2H, m), 3.4 (2H, dd), 7.1 (1H, t), 7.3–7.5 (6H, m), 7.6 (1H, d).

EXAMPLE 16

1-Butyl-7-phenyl-1H-inidole-2,3-dione

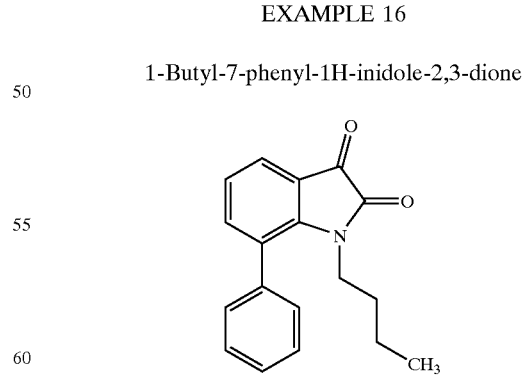

The title compound was prepared as described in Example 10 above except that 1-bromobutane was used.

$^1$H NMR: δ 0.6 (3H, t), 0.7–0.8 (2H, m), 1.1–1.3 (2H, m), 3.3 (2H, dd), 7.1 (1H, t), 7.3–7.5(6H, m), 7.6 (1H, d).

EXAMPLE 17

1-(2-Methylpropyl)-7-phenyl-1H-indole-2,3-dione

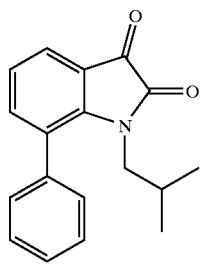

The title compound was prepared as described in Example 10 above except that 1-bromo-2-methylpropane was used.

$^1$H NMR: 0.5 (6H, d), 1.3–1.5 (H, m), 3.2 (2H, d), 7.1 (1H, t), 7.3–7.5 (6H, m), 7.6(1H, d).

EXAMPLE 18

1-Hexyl-7-phenyl-1-indole-2,3-dione

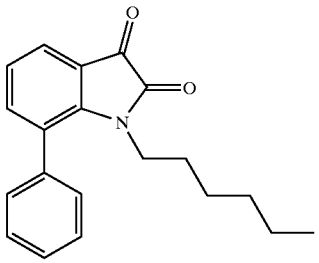

The title compound was prepared as described in Example 10 above except that 1-bromohexane was used.

$^1$H NMR: δ 0.6–0.7 (2H, m), 0.7 (3H, t), 0.8–1.0 (2H, m), 1.0–1.2 (4H, m), 3.3 (2H, dd), 7.1 (1H, t), 7.3–7.5 (6H, m), 7.6 (1H, d).

EXAMPLE 19

1-Dodecyl-7-phenyl-1H-indole-2,3-dione

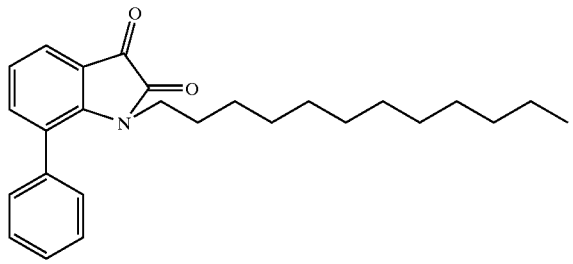

The title compound was prepared as described in Example 10 above except that 1-bromododecane was used.

$^1$H NMR: δ 0.6–0.7 (2H, m), 0.85 (3H, t), 0.9–1.4 (18H, m), 3.3 (2H, dd), 7.1 (1H, t), 7.3–7.5 (6H, m), 7.6 (1H, d).

EXAMPLE 20

1-(4-Bromobutyl)-7-phenyl-1H-indole-2,3-dione

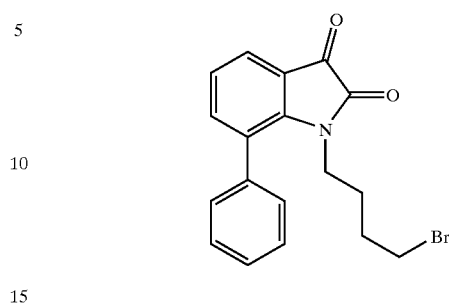

The title compound was prepared according to the process step described in the text is from Page 7, line 34 to Page 8, line 5 of WO 94/29272 using 7-phenyl-1H-indole-2,3-dione and 1,4-dibromobutane.

$^1$H NMR: δ 0.7–0.8 (2H, m), 1.1–1.3 (4H, m), 1.6–1.8 (2H, m), 3.2–3.4 (4H, m), 7.1 (1H, t), 7.3–7.5(6H, m), 7.6 (1H, d).

EXAMPLE 21

Each of the compounds of Examples 1 to 20 was assessed for bactericidal activity against *M. tuberculosis* by measuring its minimum inhibitory concentration (MIC) in the "BACTEC" (trade mark) system developed by Becton-Dickinson Diagnostic Instrument Systems, Sparks, U.S.A., which is based on a radiometric principle whereby carbon dioxide released by the catabolism of $^{14}$C-palmitate is spectrophotometrically detected and quantitated in arbitrary units of measurement referred to as growth index (GI) units.

Thus, "BACTEC" vials were inoculated with 0.1 ml of *M. tuberculosis* (final bacterial concentration, $1 \times 10^5$ colony forming units per ml) and 0.1 ml of test compound in a range of concentrations. GI values were monitored until a value of >30 was achieved for the 1:100 dilution control.

For the purpose of this test, MIC is defined as the minimum concentration of test compound that effects a >95% inhibition of the culture in comparison to the undiluted control, when the control reaches a GI value of 999.

Endpoint determination (>99% inhibition) is based on a conventional 1% resistance cut-off, wherein the organism is considered resistant to a particular concentration of test compound if growth of greater than 1% of the bacterial population is observed. Thus, a comparison is made between growth of the organism in the presence of a predetermined concentration of test compound and growth of the same organism diluted 1:100 in the absence of any test compound. The change in the GI values (ΔGI) is used to determine the endpoint susceptibility of the organism to the test compound. If the AGI of the 1:100 control is greater than the AGI in the presence of the test compound, then the concentration of test compound used is considered to be bactericidal (>99% inhibition) for the organism.

The MIC of the compounds of Examples 1 to 20 were determined for the following strains of *M. tuberculosis:*
H37Rv,
H37Ra,
1 clinical isolate susceptible to isoniazid, rifampicin, ethambutol and streptomycin [E:22/95; Estonia],
1 clinical isolate resistant to isoniazid [H:997/94; Honduras], 1 clinical isolate resistant to isoniazid and ethambutol [E:5/94; Estonia],
1 clinical isolate resistant to isoniazid and rifampicin [H:44/95; Honduras], 1 clinical isolate resistant to isoniazid and streptomycin [S: 150/96; Sweden], 1 clinical isolate resistant to isoniazid, rifampicin and streptomycin [AA:063; Ethiopia], 3 clinical isolates resistant to isoniazid, rifampicin, streptomycin and ethambutol

[P:24/95; Estonia, S:39/95; Nepal, S:42/95; China, H:1005/94; Honduras], and were found in all cases to be less than or equal to 20 $\mu$g/ml. Therefore, the compounds of Examples 1 to 20 demonstrate effective bactericidal activity against the above strains of *M. tuberculosis* which include single- and multiple-drug resistant strains.

What is claimed is:

1. A method of treating a patient suffering from, or at risk of, mycobacterial tuberculosis, which comprises administering to the patient a therapeutically effective amount of a compound of formula (I), or a pharmaceutically-acceptable salt or solvate thereof, (I)

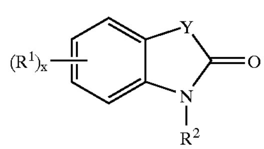

wherein x represents 0 or 1, $R^1$ represents a 3- to 7-membered (hetero)cycloalkyl group or a phenyl group, Y represents a group $CH_2$ or >C═O, and $R^2$ represents either a $C_1$–$C_{12}$ alkyl group optionally substituted by one or more halogen atoms, a group (A)

wherein m represents an integer from 3 to 7, $R^3$ represents a $C_1$–$C_6$ alkyl group and $R^4$ represents a cyclohexyl or phenyl group optionally substituted by one or more substituents selected from the group consisting of a halogen atom, $C_1$–$C_6$ alkyl and $C_1$–$C_6$ alkoxy group, or a group (B)

wherein n represents an integer from 2 to 4, p and q independently represent an integer from 1 to 2, Z represents N or CH and $R^5$ represents a cyclohexyl or phenyl group optionally substituted by one or more substituents selected from the group consisting of a halogen atom, $C_1$–$C_6$ alkyl and $C_1$–$C_6$ alkoxy group.

2. The method according to claim 1, wherein Y represents a group >C═O.

3. The method according to claim 1, wherein $R^1$ represents a 5- to 7-membered (hetero)cycloalkyl group or a phenyl group.

4. The method according to claim 1, wherein $R^1$ is located in the 5- or 7-position.

5. The method according to claim 1, wherein $R^2$ represents either a $C_4$–$C_{12}$ alkyl group, a group (A) in which $R^4$ represents a phenyl group and m and $R^3$ are as defined in claim 1, or a group (B) in which n is 2, p is 1, q is 1, Z is N or CH and $R^5$ represents a phenyl group.

6. The method according to claim 1, wherein the compound is:

5-Cyclohexyl-1-[2-[1-(phenylmethyl)-4-piperidinyl]ethyl]-1H-indole-2,3-dione;

7-Cycloheptyl-1-[2-[4-(phenylmethyl)-1-piperazinyl]ethyl]-1H-indole-2,3-dione;

5-Cyclohexyl-1-(5-(N-ethyl-N-phenylmethylamino)pentyl)-1H-indole-2,3-dione:

5-Cyclohexyl-1,3-dihydro-1-[2-[1-(phenylmethyl)-4-piperidinyl]ethyl]-2H-indol-2-one;

1-(4-(N-Ethyl-N-phenylmethylamino)butyl)-1H-indole-2,3-dione;

5-Phenyl-1-[2-[4-(phenylmethyl)-1-piperazinyl]ethyl]-1H-indole-2,3-dione;

7-Cyclopentyl-1-[2-[4-(phenylmethyl)-1-piperazinyl]ethyl]-1H-indole-2,3-dione;

5-(1-Piperidinyl)-1-[2-[4-(phenylmethyl)-1-piperazinyl]ethyl]-1H-indole-2,3-dione;

1-(4-Bromobutyl)-5-cyclohexyl-1H-indole-2,3-dione;

1-Nonyl-7-phenyl-1H-indole-2,3-dione;

1-Heptyl-7-phenyl-1H-indole-2,3-dione;

1-Octyl-7-phenyl-1H-indole-2,3-dione;

1-Decyl-7-phenyl-1H-indole-2,3-dione;

1-Undecyl-7-phenyl-1H-indole-2,3-dione;

1-Pentyl-7-phenyl-1H-indole-2,3-dione;

1-Butyl-7-phenyl-1H-indole-2,3-dione;

1-(2-Methylpropyl)-7-phenyl-1H-indole-2,3-dione;

1-Hexyl-7-phenyl-1H-indole-2,3-dione;

1-Dodecyl-7-phenyl-1H-indole-2,3-dione; or 1-(4-Bromobutyl)-7-phenyl-1H-indole-2,3-dione in the form of the free base, or a pharmaceutically acceptable salt or solvate thereof.

7. A pharmaceutical composition comprising a compound of formula (I'), (I')

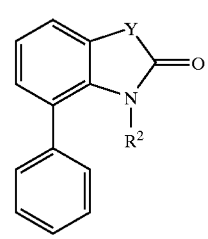

wherein Y and $R^2$ are as defined in claim 1 or a pharmaceutically-acceptable salt or solvate thereof, for the use in treatment of mycobacterial tuberculosis, in association with a pharmaceutically-acceptable adjuvant, diluent or carrier.

* * * * *